US00PP20476P2

(12) United States Plant Patent
Bowyer

(10) Patent No.: US PP20,476 P2
(45) Date of Patent: Nov. 10, 2009

(54) ***HELICHRYSUM* PLANT NAMED 'PINK SAPPHIRE'**

(50) Latin Name: *Helichrysum×amorginum*
Varietal Denomination: Pink Sapphire

(76) Inventor: Brenda Bowyer, 262 Derby Road, Chaddesden, Derby (GB) DE21 6RW ( * ) Notice: Subject to any disclaimer, the term of this patent is extended or adjusted under 35 U.S.C. 154(b) by 0 days.

(21) Appl. No.: 12/148,863

(22) Filed: Apr. 23, 2008

(51) Int. Cl.
*A01H 5/00* (2006.01)

(52) U.S. Cl. ..... Plt./359

(58) Field of Classification Search ..... Plt./359
See application file for complete search history.

*Primary Examiner*—Kent L Bell
(74) *Attorney, Agent, or Firm*—Jondle & Associates, P.C.

(57) ABSTRACT

A new *Helichrysum* plant particularly distinguished by its pink flower buds and by its good tolerance to powdery mildews, is disclosed.

2 Drawing Sheets

Genus and species: *Helichrysum×amorginum.*

Variety denomination: 'Pink Sapphire'.

BACKGROUND OF THE NEW PLANT

The present invention comprises a new and distinct cultivar of *Helichrysum,* botanically known as *Helichrysum×amorginum* and hereinafter referred to by the cultivar name 'Pink Sapphire'. The new cultivar originated from a hybridization made in Derby, Chaddesden, United Kingdom in April 2000. The female parent was the *Helichrysum* plant 'Ruby Cluster' (unpatented) while the male parent was an unnamed individual plant of *Helichrysum amorginum* (unpatented).

In March 2001 a single plant was selected for its pink flower buds. This selection was asexually propagated by vegetative cuttings and further evaluated in Derby, Chaddesden, United Kingdom to confirm the uniformity and stability of its characteristics. The present invention has been asexually propagated over three generations and has been found to retain its distinctive characteristics through successive asexual propagations.

Plant Breeder's Rights for this cultivar were applied for in the European Union on Mar. 1, 2007. 'Pink Sapphire' has not been made publicly available more than one year prior to filing of this application.

SUMMARY OF THE INVENTION

The following are the most outstanding and distinguishing characteristics of this new cultivar when grown under normal horticultural practices in Derby, Chaddesden, and Bressingham, United Kingdom.

1. Pink flower buds; and
2. Good tolerance to powdery mildews.

DESCRIPTION OF THE PHOTOGRAPHS

This new *Helichrysum* plant is illustrated by the accompanying photographs which show overall plant habit including foliage and flower buds; the colors shown are as true as can be reasonably obtained by conventional photographic procedures. The photographs are of a one-year-old plant.

DESCRIPTION OF THE NEW CULTIVAR

Figure 1:
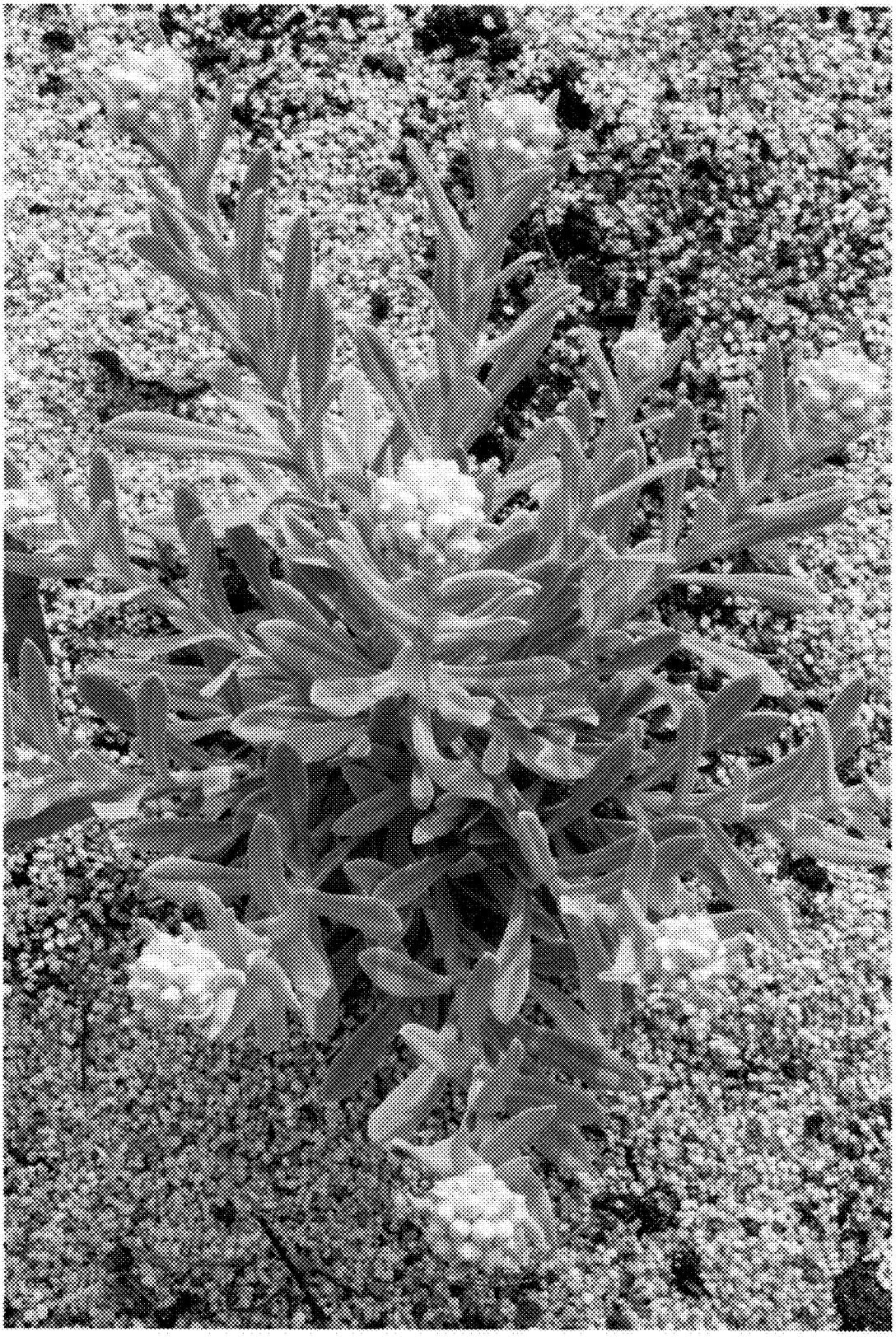
FIG. 1 shows overall plant habit including foliage and flower buds.
Figure 2:
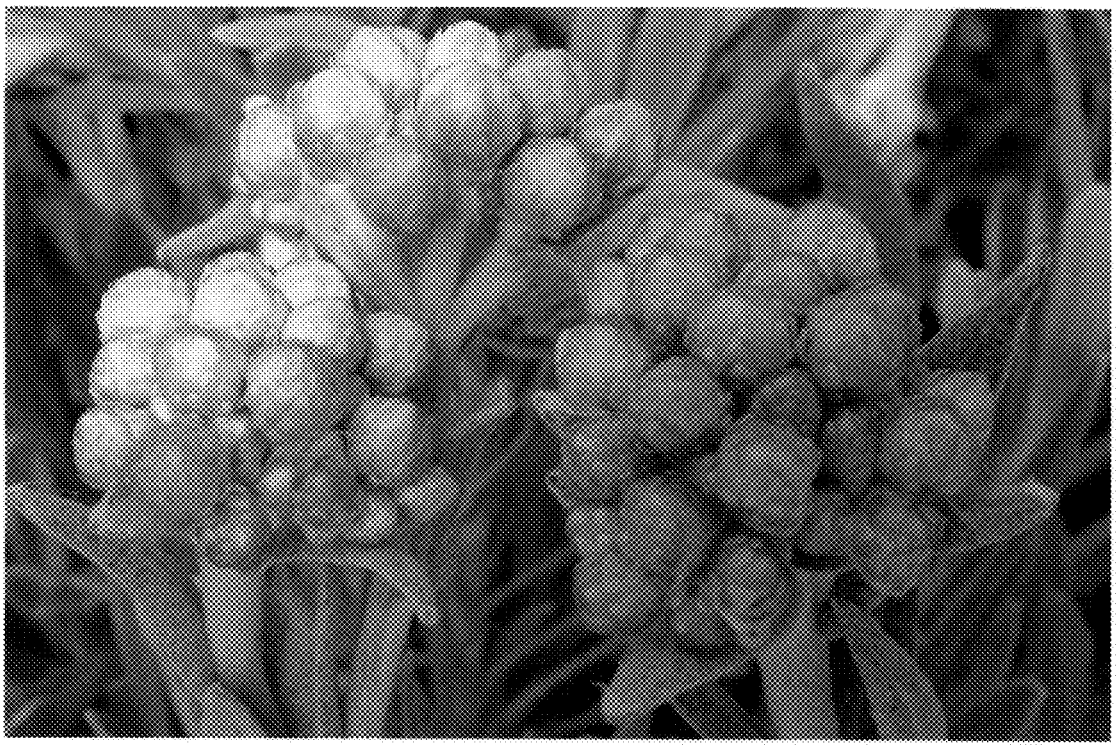
FIG. 2 shows a close-up of three clusters of flower buds.

The following detailed descriptions set forth the distinctive characteristics of 'Pink Sapphire'. The data which define these characteristics were collected from asexual reproductions carried out in Bressingham, United Kingdom. The plant history was taken on one-year-old plants grown outdoors in a 3-liter container; no growth retardants were used. The range of daytime temperatures was 80° C. to 30° C while the range of nighttime temperatures was 30° C. to 15° C. Color readings were taken outdoors under natural light. Color references are primarily to the R.H.S. Colour Chart of The Royal Horticultural Society of London (R.H.S.) (2001 edition).

DESCRIPTION OF THE NEW PLANT

Classification:

*Family.*—Asteraceae.

*Botanical.*—*Helichrysum×amorginum.*

*Common name.*—Strawflower, Everlasting flower.

Parentage:

*Female parent.*—*Helichrysum* 'Ruby Cluster' (unpatented).

*Male parent.*—An unnamed individual plant of *Helichrysum amorginum* (unpatented).

Plant:

*Habit.*—Perennial in USDA zones 8 to 10, annual in colder zones.

*Form.*—Spreading.

*Height (from top of soil, excluding flowers).*—20.0 cm to 26.0 cm.

*Width (horizontal plant diameter).*—20.0 cm to 26.0 cm.

*Propagation.*—Cuttings.

*Time to initiate and develop roots.*—15 days in summer.

*Time to produce a rooted young plant.*—70 days in summer.

*Time to produce a finished flowering plant.*—215 days.

*Root description.*—Thin, fibrous, dense, freely branching, RHS 161B (Greyed-yellow) in color.

*Keeping quality.*—Flower buds, if cut when in full color, will retain this color when dried; on the plant the flowers retain their color for about 25 days before starting to change color.

*Temperature tolerance.*—In the United Kingdom, the lowest temperature was −5° C. and the highest temperature was 30° C.

Branches or stems:

*Type* (*lateral, rosette, etc.*).—Rosette of stems arising from a woody center.

*Quantity per plant.*—Many, dense.

*Length.*—20.0 cm to 26.0 cm.

*Diameter.*—0.4 cm.

*Internode length.*—1.0 cm.

*Aspect.*—Pendulous to upright.

*Strength.*—Strong.

*Texture.*—Soft and smooth, the effect given by the dense pubescence.

*Pubescense.*—Dense, pannose.

Color.—Upper: RHS 189B (Greyed-green) and RHS 189C (Greyed-green). Lower: RHS 189C (Greyed-green).

Leaves:

*Arrangement.*—Alternate.

*Shape.*—Lanceolate.

*Color.*—Immature leaf: RHS 189C (Greyed-green). Mature leaf: Upper surface: RHS 189B (Greyed-green) and RHS 189C (Greyed-green). Lower surface: RHS 189C (Greyed-green).

*Texture* (*both surfaces*).—Pubescent.

*Length.*—6.0 cm to 8.0 cm.

*Width.*—1.5 cm.

*Apex.*—Rounded.

*Base.*—Acuminate.

*Margin.*—Entire.

*Venation pattern.*—Leaf pubescence covers both sides of leaf, no venation observed.

*Pubescence coverage of the leaf (both sides).*—Densely covers the leaf.

*Pubescence color* (*both surfaces*).—RHS 189D (Greyed-green).

*Petiole.*—Absent, amplexicaul.

Flower buds:

*Color.*—Between RHS 55A (Pink) and RHS 56C (Pink).

*Height.*—1.0 cm.

*Diameter.*—0.5 cm.

*Shape.*—Orbicular.

*Texture.*—Paper-like.

Inflorescence:

*Blooming habit* (*flowering season*).—March to May.

*Form.*—Compound umbel.

*Quantity of inflorescences on the plant.*—40 to 60.

*Lastingness of inflorescences on the plant.*—Long lasting, can be dried and will retain color as is when cut.

*Fragrance.*—Absent.

*Diameter.*—5.0 cm for entire umbel, 1.0 cm for single inflorescence

*Depth* (*height*).—4.0 cm for entire umbel, 1.0 cm for single inflorescence.

*Disc diameter.*—0.05 cm.

*Receptacle diameter.*—0.1 cm.

*Receptacle height.*—0.5 cm.

Involucral bracts or ray florets:

*Appearance.*—Papery, smooth.

*Aspect.*—Curved, upright.

*Shape.*—Obovate.

*Length.*—0.4 cm.

*Width.*—0.1 cm.

*Apex.*—Obtuse.

*Base.*—Attenuate.

*Margin.*—Entire.

*Texture.*—Papery.

*Orientation or aspect.*—Facing upward.

*Number per inflorescence.*—30 to 50.

*Color* (*when opening*).—Upper surface: RHS 55A (Red) and RHS 55B (Red). Lower surface: RHS 55C (Red).

*Color* (*when fully opened*).—Upper surface: RHS 55C (Red). Lower surface: RHS 55D (Red). Fading to RHS 155D (White) towards end of flowering period (both surfaces).

Disc florets:

*Arrangement.*—Clustered upright.

*Shape.*—Linear.

*Apex.*Acute.

*Length.*—0.1 cm.

*Width.*—0.05 cm.

*Diameter of disc.*—0.4 cm.

*Number or quantity per inflorescence.*—80 to 100.

*Base.*—Attenuate.

*Margin.*—Entire.

*Color.—Immature: RHS* 149A (Yellow-green). Mature: RHS 150D (Yellow-green). Apex: RHS 149A (Yellow-green). Mid-section: RHS 149A (Yellow-green). Base: RHS 149D (Yellow-green).

Phyllaries:

*Quantity per inflorescence.*—10 to 15.

*Length.*—0.2 cm.

*Width.*—0.2 cm.

*Shape.*—Obovate.

*Apex.*—Obtuse.

*Base.*—Attenuate.

*Margin.*—Entire.

*Texture* (*both surfaces*).—Soft.

*Color* (*both surfaces*).—RHS 189C (Greyed-green).

Peduncle:

*Length.*—1.0 cm.

*Diameter.*—0.1 cm.

*Strength.*—Strong.

*Aspect.*—Upright.

*Texture.*—Soft.

*Color.*—RHS 189C (Greyed-green).

Pedicel:

*Length.*—0.5 cm.

*Diameter.*—0.1 cm.

*Color.*—RHS 189D (Greyed-green).

Reproductive organs:

*Androecium.*—Only on disc florets. Filaments: Length: 0.2 cm. Diameter: 0.005 cm. Color: RHS 155D (White). Anthers: Shape: Cylindrical. Length: 0.1 cm. Diameter: 0.005 cm. Color: RHS 155D (White). Pollen: Amount: Sparse. Color: RHS 155D (White).

*Gynoecium.—Pistil length:* 0.2 cm. Stigma: Shape: Simple. Length: 0.005 cm. Color: RHS 155D (White). Style: Length: 0.15 cm. Color: RHS 155D (White). Ovary color: RHS 155D (White).

Seeds:

*Color.*—RHS 173D (Greyed-orange).

*Shape.*—Oval, slightly compressed, hairless.

*Length.*—0.1 cm.

*Width.*—0.1 cm.

*Quantity.*—1,000 to 3,000, seed setting is variable from year to year.

Disease and insect resistance: Good tolerance to powdery mildews; no pest problems observed.

COMPARISON WITH PARENTAL AND COMMERCIAL CULTIVARS

'Pink Sapphire' differs from the female parent 'Ruby Cluster' (unpatented) in that 'Pink Sapphire' has pink flower buds while 'Ruby Cluster' has red flower buds.

'Pink Sapphire' differs from the male parent, an unnamed individual plant of *Helichrysum amorginum* (unpatented), in that 'Pink Sapphire' has pink flower buds while the male parent has yellow flower buds.

I claim:

1. A new and distinct cultivar of *Helichrysum* plant as shown and described herein.

* * * * *